US009186428B2

(12) United States Patent
Jennings

(10) Patent No.: US 9,186,428 B2
(45) Date of Patent: Nov. 17, 2015

(54) STERILIZATION AND DECONTAMINATION OF AN ENCLOSED ENVIRONMENT

(75) Inventor: James Robert Jennings, North Yorkshire (GB)

(73) Assignee: DOW GLOBAL TECHNOLOGIES, LLC, Midland, MI (US)

( * ) Notice: Subject to any disclaimer, the term of this patent is extended or adjusted under 35 U.S.C. 154(b) by 921 days.

(21) Appl. No.: 13/256,066

(22) PCT Filed: Mar. 12, 2010

(86) PCT No.: PCT/GB2010/000470
§ 371 (c)(1),
(2), (4) Date: Nov. 28, 2011

(87) PCT Pub. No.: WO2010/103295
PCT Pub. Date: Sep. 16, 2010

(65) Prior Publication Data
US 2012/0063949 A1    Mar. 15, 2012

(30) Foreign Application Priority Data

Mar. 12, 2009 (GB) .................................. 0904269.8
Mar. 12, 2009 (GB) .................................. 0904272.2

(51) Int. Cl.
*A61L 2/20* (2006.01)
*A61L 2/24* (2006.01)
(Continued)

(52) U.S. Cl.
CPC . *A61L 2/202* (2013.01); *A61L 2/24* (2013.01); *A61L 9/015* (2013.01); *F24F 3/16* (2013.01);
(Continued)

(58) Field of Classification Search
CPC ................ A61L 2/202; A61L 9/015–9/127; A61L 2202/16; A61L 2202/25; A61L 2009/11
USPC .......... 422/3, 28, 30, 123, 124, 292–300, 305
See application file for complete search history.

(56) References Cited

U.S. PATENT DOCUMENTS

2002/0139124 A1    10/2002  Palermo
2003/0021724 A1*    1/2003  McVey ............................ 422/28
(Continued)

FOREIGN PATENT DOCUMENTS

EP    1500404 A1    1/2005
JP    9122218 A    5/1997
(Continued)

OTHER PUBLICATIONS

Examination Report issued May 7, 2013 in UK Patent Application No. GB0904269.8.
(Continued)

*Primary Examiner* — Timothy Cleveland

(57) ABSTRACT

A method of sterilization, decontamination and/or sanitation of an enclosed environment, the method comprising the steps of measuring the temperature of an enclosed environment to be treated; calculating the relative humidity required to provide a desired partial pressure at the measured temperature, the actual desired partial pressure required being based on a predetermined optimum partial pressure at a base temperature corresponding to an optimum operating temperature for that environment; introducing a predetermined quantity of water to the environment to provide the calculated relative humidity for the measured temperature; discharging ozone into the humidified environment; maintaining the ozone level at a concentration that will achieve the required degree of decontamination, sterilization and/or sanitation of the humid environment; and reducing the ozone level to an acceptable safe exposure level.

11 Claims, 1 Drawing Sheet

(51) Int. Cl.
*A61L 9/015* (2006.01)
*F24F 3/16* (2006.01)
*F24F 6/00* (2006.01)

(52) U.S. Cl.
CPC .......... *A61L 2202/11* (2013.01); *A61L 2202/16* (2013.01); *A61L 2202/25* (2013.01); *A61L 2209/11* (2013.01); *F24F 6/00* (2013.01); *F24F 2003/1664* (2013.01); *F24F 2003/1685* (2013.01)

(56) References Cited

U.S. PATENT DOCUMENTS

| 2003/0086813 | A1 | 5/2003 | Fleischer |
| 2005/0031486 | A1* | 2/2005 | Mole et al. ................. 422/28 |
| 2005/0123436 | A1 | 6/2005 | Cumberland |
| 2008/0310992 | A1 | 12/2008 | Heselton et al. |

FOREIGN PATENT DOCUMENTS

| JP | H 09122218 A | 5/1997 |
| JP | 2001-157707 A | 6/2001 |
| JP | 2001157707 A | 6/2001 |
| JP | 2001-286542 A | 10/2001 |
| JP | 2001286542 A | 10/2001 |
| JP | 2002-360675 A | 12/2002 |
| JP | 2002360675 A | 12/2002 |
| WO | 03/001119 A1 | 1/2003 |
| WO | 03101498 A2 | 12/2003 |
| WO | 2007/105099 A2 | 9/2007 |
| WO | 2008/014615 A1 | 2/2008 |
| WO | 2008014615 A1 | 2/2008 |

OTHER PUBLICATIONS

Search Report issued on Jul. 13, 2009 by the United Kingdom Intellectual Property Office in UK Patent Application No. GB0904269.8.
PCT/GB2010/000470 International Search Report, Jul. 27, 2010 (4 p.).

* cited by examiner

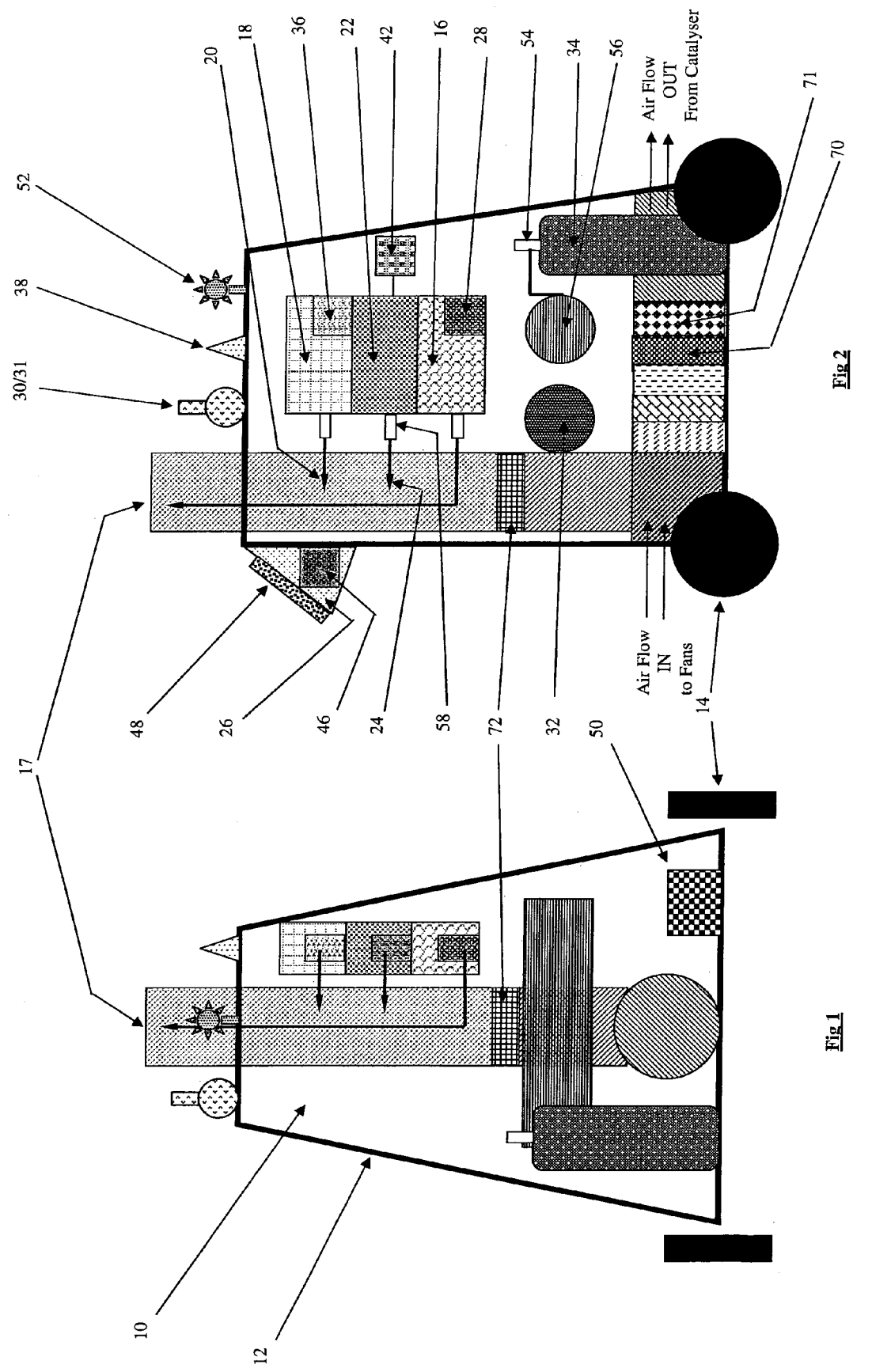

STERILIZATION AND DECONTAMINATION OF AN ENCLOSED ENVIRONMENT

CROSS-REFERENCE TO RELATED APPLICATIONS

This application is a 35 U.S.C. §371 national stage application of PCT/GB2010/000470 filed Mar. 12, 2010, which claims the benefit of British Patent Application No. 0904269.8 filed Mar. 12, 2009, and British Patent Application No. 0904272.2 filed Mar. 12, 2009, all of which are incorporated herein by reference in their entireties for all purposes.

This invention relates to a method of sterilisation, decontamination and/or sanitation, and to apparatus for use with said method.

It is a requirement to sterilise and sanitise enclosed spaces, such as kitchen areas and hospital rooms quickly and effectively, in order to destroy potentially harmful microorganisms, such as bacteria and viruses, contaminating the air and surfaces therewithin, in an acceptable timescale.

The biocidal activity of ozone is widely known and appreciated, and it is also known that the provision of ozone in a humid atmosphere increases the biocidal effectiveness.

However, problems associated with the use of ozone as a biocide have been the relatively lengthy post-treatment process to ensure that the environment is safe for returning occupants, the use of potentially environmentally damaging chemicals during the process, the general ineffectiveness of the process package in sanitising the environment, and the overall lack of simplicity of quickly setting up and using the apparatus.

The Applicant's previous application (EP 1500404, Steritrox Limited), demonstrated a method whereby the beneficial effect of ozone in a humid atmosphere could be utilised with the residual atmosphere being freed from harmful ozone within a useful timescale. The method involved the addition of an olefinic compound, such as butene-2 to the atmosphere in sufficient quantity to react with and remove all of the residual ozone. Whilst this process is efficient at providing a sterile environment, it has now been recognised that the reaction between the residual ozone and the olefinic compound leads to the production of a range of compounds, some of which have harmful properties when present in the atmosphere above a certain concentration, commonly referred to as the Occupational Exposure Level (OEL). Without prejudice to the invention, the range of compounds may include, for example, acetaldehyde, acetic acid, formaldehyde, formic acid, methanol, propionaldehyde and the like.

Additionally, the use of relative humidity to define the water content of the atmosphere for the reaction is very imprecise because the water content changes at a given relative humidity as the temperature changes. This often results in more water than is actually required being provided in the atmosphere. This can lead to condensation of water on surfaces acting as a barrier to the reaction and may also result in a damp room when the treatment has been completed. This is clearly undesirable. A further concern with very high humidity levels is that ozone is hydrolysed to hydrogen peroxide, which is known to be toxic.

The present invention seeks to provide a solution to these problems, in particular to provide a sterilisation and decontamination process and apparatus of increased efficiency by optimising the water content required for the satisfactory performance of the process and apparatus.

According to a first aspect of the present invention, there is provided a method of sterilisation, decontamination and/or sanitation of an enclosed environment, the method comprising the steps of:
a) measuring the temperature of an enclosed environment to be treated;
b) calculating the relative humidity required to provide a predetermined desired partial pressure at the measured temperature, the actual desired partial pressure being based on an optimum partial pressure at a base temperature;
c) introducing an appropriate quantity of water to the environment to provide the calculated relative humidity within the enclosed environment for the measured temperature;
d) discharging ozone into the humidified environment;
e) maintaining the ozone level at a concentration that will achieve the required degree of decontamination, sterilisation and/or sanitation of the humid environment; and
f) reducing the ozone level to an acceptable safe exposure level.

Preferably, the predetermined desired partial pressure is at least 4.0 Torr at the measured temperature.

The level of ozone may be reduced by natural decomposition and/or assisted decomposition such as catalytic decomposition, photochemical deposition or quenching with an unsaturated hydrocarbon. More preferably, the method includes the step of passing the decontaminated and sterilised environment through a catalyst to reduce the concentration of ozone to a predetermined amount; introducing a hydrocarbon containing a carbon-carbon double bond into the environment to react preferentially with the discharged ozone; and recycling the decontaminated and sterilised environment through the catalyst until the concentration of harmful products falls to a safe level.

Preferably, the method continuously monitors the temperature of the environment and automatically adjusts the discharge of water into the environment to maintain the desired partial pressure of water in the environment at the given temperature.

The required relative humidity for a particular temperature is derived from an optimum relative humidity at a base temperature. In the present invention, the base temperature will depend upon the operating temperature of the enclosed environment. For example, cool environments such as food preparations areas, will have a lower optimum operating temperature than warmer environments, such as hospital wards.

The required relative humidity for a particular operating temperature is derived from an optimum relative humidity at a base temperature and the base temperature preferably corresponds to the optimum operating temperature for the environment to be treated (as opposed to the actual measured temperature of the environment).

The required relative humidity is preferably computed by means of an algorithm comprising the steps of determining the partial pressure of water at the optimum operating temperature and the optimum relative humidity to provide a base partial pressure; determining the saturated vapour pressure for the measured temperature; and calculating the required relative humidity as a function of the saturated vapour pressure and the base partial pressure.

In one embodiment of the present invention there is provided a method of sterilisation, decontamination and/or sanitation of a cool environment up to 15° C., such as a food preparation area, the method comprising the steps of:
c) measuring the temperature of an enclosed environment to be treated;

d) calculating the relative humidity required to provide a desired partial pressure of 4.0 to 10.99 torr at the measured temperature, the actual desired partial pressure being based on a predetermined optimum partial pressure at a base temperature;

c) introducing an appropriate quantity of water to the environment to provide the calculated relative humidity within the enclosed environment for the measured temperature;

d) discharging ozone into the humidified environment;

e) maintaining the ozone level at a concentration that will achieve the required degree of decontamination, sterilisation and/or sanitation of the humid environment; and f) reducing the ozone level to an acceptable safe exposure level.

In this embodiment of the present invention, the preferred base temperature is 6° C., being the optimum temperature of a cold food store, and the preferred optimum relative humidity for this temperature is 90% by volume, providing a preferred base partial pressure of 6.3 torr. The required relative humidity is preferably computed by means of an algorithm comprising the steps of determining the partial pressure of water at 6° C. and 90% relative humidity to provide a base partial pressure; determining the saturated vapour pressure for the measured temperature and calculating the required relative humidity as a function of the saturated vapour pressure at the measured temperature and the base partial pressure.

It is to be appreciated that other cool operating environments may be kept at optimum temperatures above or below 6° C. and the base partial pressure could be adjusted accordingly. However, at temperatures below 1-2° C. it is unlikely that the process will operate effectively due to freezing of the water droplets.

In another embodiment of the present invention, there is provided a method of sterilisation, decontamination and/or sanitation of a warm environment at or above 15° C., such as a hospital ward, the method comprising the steps of:

e) measuring the temperature of an enclosed environment to be treated;

f) calculating the relative humidity required to provide a desired partial pressure of at least 11.00 torr at the measured temperature, the actual desired partial pressure being based on a predetermined optimum partial pressure at a base temperature;

c) introducing an appropriate quantity of water to the environment to provide the calculated relative humidity within the enclosed environment for the measured temperature;

d) discharging ozone into the humidified environment;

e) maintaining the ozone level at a concentration that will achieve the required degree of decontamination, sterilisation and/or sanitation of the humid environment; and f) reducing the ozone level to an acceptable safe exposure level.

In this embodiment, the preferred base temperature is 18° C., and the preferred predetermined relative humidity for this temperature is 90% by volume, providing a preferred base partial pressure of 13.9 torr. The required relative humidity is preferably computed by means of an algorithm comprising the steps of determining the partial pressure of water at 18° C. and 90% relative humidity to provide a base partial pressure; determining the saturated vapour pressure for the measured temperature and calculating the required relative humidity as a function of the saturated vapour pressure at the measured temperature and the base partial pressure.

According to a second aspect of the present invention, there is provided a sterilisation, decontamination and/or sanitation apparatus for use with a method in accordance with the first aspect of the present invention, the apparatus comprising a temperature sensor, a humidifier unit, an ozone discharge unit, and a controller by which the humidifier unit and ozone discharge unit are controllable based on predetermined conditions, the humidifier unit being automatically controlled to vary the amount of water introduced into an environment based on the temperature measured by the temperature sensor to provide a predetermined desired partial pressure, the actual partial pressure being based on a predetermined optimum partial pressure at a base temperature.

In a preferred embodiment of the present invention, the apparatus includes an ozone depletion catalyst and/or a hydrocarbon discharge unit.

The apparatus includes appropriate software for calculating the amount of water to be introduced into the environment based on the temperature measured and the base partial pressure to provide the calculated relative humidity.

The invention will now be more specifically described with reference to the following examples in which Examples 1 and 2 relate to the sterilisation and decontamination of a cool environment using the process and apparatus of the present invention and Examples 3 and 4 relate to the sterilisation and decontamination of a warm environment using the process and apparatus of the present invention, and by to the accompanying drawings, in which:

FIG. 1 is a diagrammatic side elevational view of one embodiment of sterilisation and decontamination apparatus for carrying out the process of the invention; and FIG. 2 is a diagrammatic front view of the apparatus shown in FIG. 1;

The process and apparatus of the present invention use ozone at increased humidity levels for the sterilisation and decontamination of an enclosed environment such as food preparation areas or a hospital ward. Any degree of condensation within the enclosed environment as a result of this increased humidity is clearly undesirable. Therefore, the quantity of water deployed to maintain a satisfactory degree of humidification must not be such as to saturate the atmosphere with water vapour. In relation to healthcare environments, there is clearly a need to keep the fabric of the room and its contents dry. Puddles of any condensed water would have to be removed after the process had finished which would inevitably require mopping up. This is likely to reintroduce bacterial infection into the room. Additionally any equipment in the room, such as TV's and curtains, need to kept dry to remove the need for inconvenient and deleterious drying out of these items prior to re-use of the room.

In a typical food preparation area, the temperature is usually kept below approximately 6° C. to reduce possible deterioration of the food. A typical level of humidity that has been found to give satisfactory results is 90% at a temperature of 6° C. At this temperature, the partial pressure of water is 6.3 torr, based on the saturated water vapour pressure being 7.00 Torr at this temperature. If the temperature were to rise above 6° C., then it would be possible to operate with a higher vapour pressure of water without detriment to the process, but this would not necessarily lead to any increase in the degree of sterilisation or decontamination that would be achieved. Previously, the use of ozone for the decontamination and/or sterilisation of an area has been linked solely to the relative humidity as a means for defining the water content of the area to be treated. However, this is very imprecise and often results in too high a water content being provided for the reaction. The process and apparatus of the present invention measure the temperature of the area to be treated prior to and during the introduction of the ozone and calculate the relative humidity required for that particular temperature to correspond to a relative humidity of 90% at 6° C., as detailed below.

At a temperature of 6° C. the saturated vapour pressure of water is 7.0 torr (approximately 7 mm Hg pressure). Thus, for a process that requires 90% relative humidity at 6° C., the partial pressure of water needs to be a minimum of 6.3 torr.

As the temperature rises, the saturated vapour pressure of water rises, approximately in accordance with Equation 1 below:

$$\text{Log}_{10} P_T = 8.07131 - (1730.61/(233.426 + T^\circ \text{C.})) \quad [\text{Equation 1}]$$

where $P_T$ is the saturated vapour pressure and T is the temperature in degrees Celsius.

The required relative humidity (RH) is then calculated using Equation 2 below:

$$\text{RH} = (6.3 \ast 100)/P_T$$

where $P_T$ is again the saturated vapour pressure at temperature T° C.

The figure 6.3 torr is derived from a base temperature of 6° C. If the base temperature for a specific situation is different to 6° C., then a different multiplier must be calculated from the saturated vapour pressure of water at that temperature, and the required relative humidity.

The calculated relative humidity is then fed back automatically to enable control over the amount of water introduced into the environment for that given temperature. Thus, the process and apparatus is automatically adjusted to operate at a lower relative humidity when the temperature rises, thereby reducing the amount of excess water present in the atmosphere which can have a detrimental effect on the reaction and the feel of the environment.

EXAMPLE 1

The optimum relative humidity for carrying out the decontamination process in a food store at 6° C. is 90% by volume. However, the measured temperature of the food store is 8° C. The saturated vapour pressure using Equation 1 above is 8.00 torr. Therefore, the relative humidity required to provide a partial pressure of water of 6.3 torr is 78.7%.

Thus, at 8° C., the area needs to be subjected to the lower relative humidity of 78.7% rather than 90%.

EXAMPLE 2

A food store is kept at 3° C. and a typical relative humidity found to give satisfactory results for the process of the present invention is 85% at this temperature. The saturated vapour pressure of water at this temperature is 5.64 torr and therefore the base partial pressure is 4.79 torr. If the temperature of the store rises to 4° C., a relative humidity level of 79% will be required.

The method and apparatus of the present invention therefore measures the temperature of the environment to be treated, calculates the saturated vapour pressure of water at that temperature according to Equation 1 above, calculates the required RH from Equation 2 above and, feeds this back by means of an intelligent control system to control the amount of water introduced into the environment for that particular temperature to maintain the required relative humidity at that temperature.

In a typical healthcare environments, such as hospital operating theatres and wards, the temperature is usually kept above approximately 15° C., normally above 18° C. A typical level of humidity that has been found to give satisfactory results is 90% at a temperature of 18° C. At this temperature, the partial pressure of water is 13.9 torr, based on the saturated water vapour pressure being 15.4 Torr at this temperature. If the temperature were to rise above 18° C., then it would be possible to operate with a higher vapour pressure of water without detriment to the process, but this would not necessarily lead to any increase in the degree of sterilisation or decontamination that would be achieved. Similarly, if the temperature was to fall below 18° C., for example, to 16° C., it would be necessary to work with a lower vapour pressure of water, to avoid condensation.

At a temperature of 18° C. the saturated vapour pressure of water is 15.4 torr (approximately 16 mm Hg pressure). Thus, for a process that requires 90% relative humidity at 18° C., the partial pressure of water needs to be a minimum of 13.9 torr.

As the temperature rises, the saturated vapour pressure of water rises, approximately in accordance with Equation 1 below:

$$\text{Log}_{10} P_T = 8.07131 - (1730.61/(233.426 + T^\circ \text{C.})) \quad [\text{Equation 1}]$$

where $P_T$ is the saturated vapour pressure and T is the temperature in degrees Celsius.

The required relative humidity (RH) is then calculated using Equation 3 below:

$$\text{RH} = (13.9 \ast 100)/P_T \quad [\text{Equation 3}]$$

where $P_T$ is again the saturated vapour pressure at temperature T° C.

The figure 13.9 torr is derived from a base temperature of 18° C. If the base temperature for a specific situation is different to 18° C., then a different multiplier must be calculated from the saturated vapour pressure of water at that temperature, and the required relative humidity.

The calculated relative humidity is then fed back automatically to enable control over the amount of water introduced into the environment for that given temperature. Thus, the process and apparatus is automatically adjusted to operate at a lower relative humidity when the temperature rises, thereby reducing the amount of excess water present in the atmosphere which can have a detrimental effect on the reaction and the feel of the environment.

EXAMPLE 3

The optimum relative humidity for carrying out the decontamination process at 18° C. is 90% by volume. At a temperature of 18° C., the saturated vapour pressure of water is 15.4 torr (approximately 16 mm Hg). Thus, for a process that requires 90% relative humidity at 18° C., the partial pressure of water needs to be a minimum of 13.9 torr at 18° C.

EXAMPLE 4

Following on from Example 1 above, the temperature of a hospital ward is found to be 20° C. Using Equation 1 and Equation 2 above, the relative humidity required in the room for optimum operation of the process can be calculated as follows:

$$\text{Log}_{10} P_T = 8.07131 - (1730.61/(233.426 + T^\circ \text{C.})) \quad [\text{Equation 1}]$$

where $P_T$ is the saturated vapour pressure and T is the temperature in degrees Celsius.

The required relative humidity can then be calculated using equation 3:

$$\text{RH} = (13.9 \ast 100)/P_T \quad [\text{Equation 3}]$$

where $P_T$ is again the saturated vapour pressure at temperature T° C.

$P_T$ works out as 17.50 torr at 20° C. The relative humidity required to give a partial pressure of water of 13.9 torr then becomes 84.7% at the higher temperature. Thus, we can operate at a lower relative humidity when the temperature rises.

Referring now to the accompanying drawings, there is shown an example of a sterilisation and decontamination apparatus 10 for carrying out the present invention. The apparatus comprises a portable enclosure 12 which can be opened and which, in use, generates a positive pressure within the interior to protect sensitive devices within the enclosure from the deleterious affects of ozone. However, it is to be appreciated that alternative means could be provided to protect the internal sensitive components from being damaged by the ozone. The enclosure 12 has wheels 14 and houses a humidifier unit 16 having a humidified air outlet 17, an ozone discharge unit 18 having an ozone discharge outlet 20, a vessel containing an ozone catalyst 70, a hydrocarbon discharge unit 22 having a hydrocarbon discharge outlet 24, a temperature sensor 31 and a control unit 26.

The illustrated example has an ozone depletion catalyst but alternative suitable ozone depletion means may be used in the present invention, such as photochemical means.

The humidifier unit 16 in the illustrated example includes a humidifier 28, a humidistat sensor 30, a temperature sensor 31 and a water reservoir 34. If an ultrasonic humidifier is used, a compressed air supply also needs to be provided, for example, in the form of a compressed air tank or container housed within the enclosure 12. The compressed air tank is connected to the water reservoir 34 and the humidifier 28. Water droplets having a diameter of less that 5 microns, preferably 2-3 microns, are introduced into the air to enhance the rate of evaporation into the atmosphere.

The ozone discharge unit 18 includes an ozone generator 36, an ozone detector sensor 38, and an oxygen supply 56 for supplying oxygen to the ozone generator 36. Oxygen is preferred to air for the generation of ozone because this avoids the formation of toxic oxides of nitrogen, increases the rate at which the required concentration of ozone is achieved and also increases the yield of ozone.

The ozone catalyst 70 is any suitable catalyst that is able to remove ozone from the atmosphere. The catalyst may be selected from a range of proprietary substances that are known to be active in the catalytic decomposition of ozone. Such catalysts may optionally contain platinum group metals, oxides of manganese, and other substances which may have a promoting effect.

The hydrocarbon discharge unit 22 includes a hydrocarbon supply 42 in the form of a tank or container containing a volatile unsaturated hydrocarbon, such as butene. Preferably, the butene is butene-2. However, the hydrocarbon can be any suitable hydrocarbon having a carbon-carbon double bond, for reasons which will become apparent hereinafter. The hydrocarbon is selected based on its speed of reaction with ozone and the toxicology of its decay products.

The control unit 26 controls the apparatus 10 and is preset with at least one sterilisation and decontamination routine. The control unit 26 includes a controller 46 and a user interface 48 by which a user can input commands to the apparatus 10.

The apparatus 10 may include an on-board battery 50 and/or may be connectable to a mains power supply. In the case of the on-board battery 50, the battery is preferably rechargeable. If a mains-operated apparatus is provided, this may have a battery back-up system to enable the machine to failsafe in the event of a mains power failure.

The apparatus 10 will also typically include other safety features, such as safety sensors, and software routines to prevent start-up or initiate shut-down in the event of a system failure.

In use, the apparatus 10 is first located in the area which is to be sterilised and decontaminated. The power to the apparatus 10 is switched on, and the control unit 26 undertakes an initial safety check. If the safety check is not passed, the apparatus 10 does not operate and outputs a suitable indication using warning lights 52. During the process, safety checks are made continuously and, in the event of a system failure, the system defaults to a safe mode.

The temperature of the environment is continuously monitored and the relative humidity to provide a desired partial pressure (generally at least 4 torr) at that temperature is calculated automatically by the control unit with a predetermined volume of water being introduced into the environment to achieve that humidity level. The volume is adjusted accordingly upon detection of a temperature change.

The temperature of the humidified air is above the dew point of the environment, and thus condensation does not occur.

The controller 46 continues to monitor the ozone level, the relative humidity through the humidistat sensor 30 and the ambient temperature through the thermocouple 31. If after a predetermined interval of time, for example 10 minutes, the required relative humidity level (as calculated by reference to the measured temperature and partial pressure of water at the optimum operating base temperature) has not been reached and/or the required ozone level has not been obtained, the controller 46 aborts the sterilisation and decontamination routine and provides a suitable indication.

Oxygen is supplied to the ozone generator 36, and ozone is generated. The generated ozone is then fed into the discharging humidified airstream. The controller 46 provides a suitable indication that the ozone generator 36 is operating, and monitors the ambient ozone levels through the ozone detector sensor 38.

Both the ozone and water vapour concentration to be detected can be altered. Once the preset ozone and water vapour levels have been detected within the allotted interval, the controller 46 enters a timing phase, known as the "dwell time".

The dwell time can also be altered, for example, to one hour, and will depend on the degree and/or type of decontamination/sterilisation to be provided. For instance, contamination by spores or moulds, such as *clostridium difficile*, generally require a longer dwell time than contamination by bacteria, such as *listeria* and methicillin resistant *staphylococcus aureus* (MRSA).

During the dwell time, the ozone concentration and relative humidity are continuously monitored. If the ozone level falls below a predetermined threshold, the ozone discharge unit 18 is reactivated to replenish the ozone levels. If the relative humidity level falls below the calculated value, the humidifier unit 16 is reactivated to restore the water vapour level.

Again, during the reactivation period, should either the ozone concentration or the relative humidity fail to reach the above-mentioned predetermined minima within a set time interval, for example 10 minutes, the controller 46 aborts the sterilisation and decontamination routine and outputs a suitable indication.

After the dwell time has elapsed, the controller 46 closes the compressed air valve 54 and the oxygen supply valve 56, and the humidifier unit 16 and the ozone discharge unit 18 are switched off. An electric fan 71 then blows the atmosphere through the catalyst 70 to reduce the levels of ozone; the level of ozone being monitored continuously. When the concentration of the ozone has fallen to the required level, such as 8 mg m$^{-3}$ an unsaturated hydrocarbon is introduced by means of a hydrocarbon discharge valve 58 of the hydrocarbon discharge unit 22. The concentration of ozone is continuously monitored and seen to fall to an undetectable level. The catalyst 70 may be continuously deployed until the concentration of ozone falls below its OEL.

When the ozone detector sensor 38 detects that the ozone concentration levels are less than a predetermined value, for example 0.2 ppm or less, the controller 46 closes the hydrocarbon discharge valve 58 and outputs an indication that the sterilisation and decontamination routine is complete. The ozone level of 0.2 ppm, depending on the size of the area being sterilised and decontaminated, is usually achieved within 3 to 4 minutes. The apparatus may include a feedback ozone measurement system (not shown) to determine the quantity of hydrocarbon added to the environment thereby reducing the chance of overdosing the hydrocarbon input and associated potential toxicology issues.

If the ozone detector sensor 38 fails to indicate that the predetermined safe level of ozone has been reached within a predetermined time interval, for example 10 minutes, the controller 46 outputs an indication warning of potentially hazardous ozone levels in the room. The controller may be programmed to allow a time interval to pass in excess of the standard half-life of ozone before announcing that the room may be re-occupied.

It is envisaged that the sterilisation and decontamination apparatus may be integrally formed as part of an area, or may be only partly portable. For example, the compressed air supply and/or oxygen supply could be integrally formed as part of the area to be regularly sterilised and decontaminated. Alternatively, components could be housed within the enclosure of the apparatus. In this case, the required supply could be linked to the apparatus via a detachable umbilical pipe. The machine may also consist of a main unit and a wirelessly connected remote controller wherein the or each preset routine may be remotely initiated by a user from outside the area to be sterilised and decontaminated.

Although the oxygen supply is typically in the form of one or more oxygen tanks or cylinders, a commercially available oxygen concentrator can be used.

The apparatus uses an electric fan 72 as a gas movement device to circulate the ambient air, ozone and hydrocarbon. However, depending on the particular application, an air mover may be used instead of an electric fan.

The above-described apparatus utilises a method of producing an artificially high level of non-condensing humidity, and generating in-situ a high concentration of ozone.

The materials of the apparatus are resistant to the corrosive effects of ozone and high humidity, and the solvent effects of the hydrocarbon.

The condition of all the valves are monitored using integrally incorporated sensors connected to the controller. The valves failsafe to an appropriate position, such as the closed position so that user safety is maintained at all times.

The controller may also incorporate a tamper proof recording system to monitor use, time, date, operational success/failure and other parameters required, to measure performance of the machine.

It is thus possible to provide a method and apparatus for providing a degree of sterilisation, decontamination and/or sanitation which is fast, effective and does not provide harmful byproducts above a recommended safety level for the environment concerned. Furthermore, the fine tuning of the method and apparatus to take account of the actual temperature of the area to be treated such that only the required volume of water is introduced into the area results in increased efficiency. Less condensation will occur on surfaces which can act as a barrier to the biocidal activity and the longevity of any catalyst should be improved as high concentrations of water vapour are detrimental to the performance of the catalyst. The reduced water content will also give the premises a higher comfort feel due to reduced dampness. Less puddling caused by condensation also reduces the need to dry out the room prior to re-occupation. The apparatus may be discrete and portable. The method provides better than 99.99% effective sterilisation and decontamination of an area without impacting the environment with harmful by-products. Rapid re-use of a contaminated area can thus be realised.

The embodiments described above are given by way of examples only, and other modifications will be apparent to persons skilled in the art without departing from the scope of the invention as defined by the appended claims.

The invention claimed is:

1. A method of sterilisation, decontamination and/or sanitation of an enclosed environment, the method comprising:
measuring the temperature of the enclosed environment to be treated;
calculating a first relative humidity that results in a predetermined partial pressure of water vapour at the measured temperature, the first relative humidity calculated as a function of the predetermined partial pressure derived from a predetermined second relative humidity at a base temperature predetermined for the enclosed environment and a saturated vapour pressure at the measured temperature;
introducing an amount of water to the environment to provide the first relative humidity; and then
discharging ozone into the enclosed environment;
maintaining the ozone level at a concentration that will achieve a predetermined degree of decontamination, sterilisation and/or sanitation of the enclosed environment; and
reducing the ozone level to a predetermined exposure level.

2. A method as claimed in claim 1 further comprising reducing the ozone level by natural or assisted decomposition.

3. A method as claimed in claim 1 further comprising passing the decontaminated and/or sterilised environment through a catalyst to reduce the concentration of ozone to a predetermined amount.

4. A method as claimed in claim 2 further comprising introducing a hydrocarbon containing a carbon-carbon double bond into the environment to react preferentially with the discharged ozone.

5. A method as claimed in claim 1 further comprising automatically adjusting the amount of water introduced into the environment upon detection of a change in temperature of the enclosed environment to maintain the predetermined partial pressure of water vapour in the environment.

6. A method as claimed in claim 1 wherein the base temperature is 18° C. and the base partial pressure is 13.9 Torr.

7. A method as claimed in claim 1 wherein the base temperature is 15° C. and the base partial pressure is 11.4 Torr.

8. A method as claimed in claim 1 wherein the base temperature is 6° C. and the base partial pressure is 6.3 Torr.

9. A method as claimed in claim 1 wherein maintaining the ozone level at the concentration that will achieve the predetermined degree of decontamination, sterilisation and/or sanitation of the enclosed environment further comprises maintaining the level of ozone in the range 1-100 ppm v/v.

10. The method as claimed in claim 1 wherein the predetermined second relative humidity is 90%.

11. The method as claimed in claim 3 further comprising introducing a hydrocarbon containing a carbon-carbon double bond into the environment to react preferentially with the discharged ozone.

* * * * *